(12) United States Patent
Zhang et al.

(10) Patent No.: US 9,908,908 B2
(45) Date of Patent: Mar. 6, 2018

(54) TENOFOVIR PRODRUG AND PHARMACEUTICAL USES THEREOF

(71) Applicant: Jiangsu Hansoh Pharmaceutical Co., Ltd., Lianyungang, Jiangsu (CN)

(72) Inventors: Fuyao Zhang, Shanghai (CN); Dong Wei, Shanghai (CN)

(73) Assignee: Jiangsu Hansoh Pharmaceutical Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 14/423,182

(22) PCT Filed: Jul. 10, 2013

(86) PCT No.: PCT/CN2013/079123
§ 371 (c)(1),
(2) Date: Feb. 23, 2015

(87) PCT Pub. No.: WO2014/032481
PCT Pub. Date: Mar. 6, 2014

(65) Prior Publication Data
US 2015/0225433 A1 Aug. 13, 2015

(30) Foreign Application Priority Data

Aug. 30, 2012 (CN) .......................... 2012 1 0315565
Feb. 1, 2013 (CN) .......................... 2013 1 0041647

(51) Int. Cl.
| C07D 403/02 | (2006.01) |
| A61K 31/4188 | (2006.01) |
| A61K 31/4985 | (2006.01) |
| A61K 31/675 | (2006.01) |
| C07F 9/6561 | (2006.01) |

(52) U.S. Cl.
CPC ........ *C07F 9/65616* (2013.01); *A61K 31/675* (2013.01)

(58) Field of Classification Search
CPC .............. C07D 403/02; C07F 9/65616; A61K 31/4188; A61K 31/4985; A61K 31/675
USPC ........................................... 514/810; 544/244
See application file for complete search history.

(56) References Cited

U.S. PATENT DOCUMENTS

| 5,278,153 A | 1/1994 | Biller |
| 5,545,750 A | 8/1996 | Kempf et al. |
| 5,670,675 A | 9/1997 | Kempf et al. |
| 5,717,095 A | 2/1998 | Arimilli et al. |
| 5,731,432 A | 3/1998 | Edon et al. |
| 5,733,788 A | 3/1998 | Bischofberger |
| 5,789,394 A | 8/1998 | Nguyen-Ba et al. |
| 5,798,340 A | 8/1998 | Bischofberger et al. |
| 5,854,228 A | 12/1998 | Webb, II et al. |
| 5,874,577 A | 2/1999 | Chen et al. |
| 5,886,179 A | 3/1999 | Arimilli et al. |
| 5,977,061 A | 11/1999 | Holy et al. |
| 6,005,107 A | 12/1999 | Nguyen-Ba et al. |
| 6,228,861 B1 | 5/2001 | Nagarathnam et al. |
| 6,331,543 B1 | 12/2001 | Garvey et al. |
| 6,455,513 B1 | 9/2002 | McGuigan et al. |
| 6,465,649 B1 | 10/2002 | Gutierrez et al. |
| 6,489,476 B1 | 12/2002 | Dang et al. |
| 6,653,296 B1 | 11/2003 | Holy et al. |
| 6,756,360 B1 | 6/2004 | Erion et al. |
| 7,300,924 B2 | 11/2007 | Boojamra et al. |
| 7,390,791 B2 | 6/2008 | Becker et al. |
| 7,439,350 B2 | 10/2008 | Bischofberger et al. |
| 7,951,787 B2 | 5/2011 | McGuigan |
| 8,835,630 B1 | 9/2014 | Hostetler et al. |
| 8,946,243 B2 | 2/2015 | Margolis et al. |
| 2002/0035155 A1 | 3/2002 | Kaddurah-Daouk |
| 2003/0050251 A1 | 3/2003 | Semple et al. |
| 2003/0144283 A1 | 7/2003 | Coleman et al. |
| 2003/0236227 A1 | 12/2003 | Druzgala et al. |
| 2004/0002475 A1 | 1/2004 | Hakimelahi |
| 2005/0080078 A1 | 4/2005 | Aquila et al. |
| 2005/0148623 A1 | 7/2005 | DeGoey et al. |

(Continued)

FOREIGN PATENT DOCUMENTS

| CN | 1425680 A | 6/2003 |
| CN | 1465582 A | 1/2004 |

(Continued)

OTHER PUBLICATIONS

Cihlar, Tomas "Amidate Prodrugs of Nucleotide Phosphonates: From Design to In vivo Proof of Concept" Collect. Symp. Series (2008), 10: pp. 45-53.*

(Continued)

*Primary Examiner* — Matthew Coughlin
*Assistant Examiner* — Sagar Patel
(74) *Attorney, Agent, or Firm* — Panitch Schwarze Belisario & Nadel LLP

(57) ABSTRACT

The invention relates to a tenofovir prodrug and pharmaceutical uses thereof. In particular, the invention relates to a compound as shown in general formula (I):

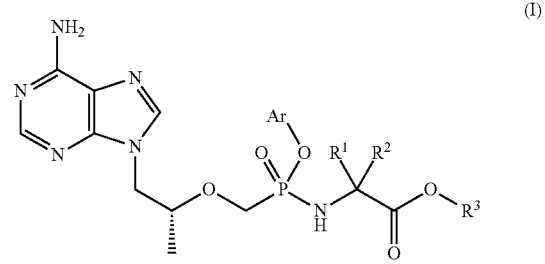

and its isomer, pharmaceutically acceptable salt, hydrate or solvate, as well as their uses in preparing drugs for treating viral infectious diseases, especially HIV infection, hepatitis B, or diseases caused by hepatitis B virus, wherein the definition of each substituent in the general formula (I) is as defined in the specification.

16 Claims, No Drawings

(56) References Cited

U.S. PATENT DOCUMENTS

| | | |
|---|---|---|
| 2005/0215612 A1 | 9/2005 | Kuo et al. |
| 2006/0030545 A1 | 2/2006 | Cheng et al. |
| 2006/0046981 A1 | 3/2006 | Shibata |
| 2009/0163712 A1 | 6/2009 | Guo et al. |
| 2013/0210757 A1 | 8/2013 | Huang et al. |
| 2014/0256684 A1 | 9/2014 | Beard et al. |
| 2014/0256685 A1 | 9/2014 | Beard et al. |
| 2014/0288025 A1 | 9/2014 | Milne et al. |
| 2014/0315790 A1 | 10/2014 | Bushell et al. |

FOREIGN PATENT DOCUMENTS

| | | |
|---|---|---|
| CN | 1523028 A | 8/2004 |
| CN | 1583769 A | 2/2005 |
| CN | 1634943 A | 7/2005 |
| CN | 1796393 A | 7/2006 |
| CN | 1810816 A | 8/2006 |
| CN | 1966514 A | 5/2007 |
| CN | 1984640 A | 6/2007 |
| CN | 1986553 A | 6/2007 |
| CN | 101003550 A | 7/2007 |
| CN | 101066980 A | 11/2007 |
| CN | 101066981 A | 11/2007 |
| CN | 101085785 A | 12/2007 |
| CN | 101089004 A | 12/2007 |
| CN | 101143879 A | 3/2008 |
| CN | 101190927 A | 6/2008 |
| CN | 101190935 A | 6/2008 |
| CN | 101230065 A | 7/2008 |
| CN | 101278938 A | 10/2008 |
| CN | 101279987 A | 10/2008 |
| CN | 101307076 A | 11/2008 |
| CN | 101418017 A | 4/2009 |
| CN | 101450954 A | 6/2009 |
| CN | 101463045 A | 6/2009 |
| CN | 101475594 A | 7/2009 |
| CN | 101531679 A | 9/2009 |
| CN | 101531680 A | 9/2009 |
| CN | 101574356 A | 11/2009 |
| CN | 101585854 A | 11/2009 |
| CN | 101591357 A | 12/2009 |
| CN | 101648974 A | 2/2010 |
| CN | 101659676 A | 3/2010 |
| CN | 101712692 A | 5/2010 |
| CN | 101759722 A | 6/2010 |
| CN | 101781334 A | 7/2010 |
| CN | 101781335 A | 7/2010 |
| CN | 101870713 A | 10/2010 |
| CN | 1947796 B | 11/2010 |
| CN | 101906119 A | 12/2010 |
| CN | 101928302 A | 12/2010 |
| CN | 101948485 A | 1/2011 |
| CN | 101985454 A | 3/2011 |
| CN | 102040626 A | 5/2011 |
| CN | 102060876 A | 5/2011 |
| CN | 102070670 A | 5/2011 |
| CN | 102093417 A | 6/2011 |
| CN | 102276667 A | 12/2011 |
| CN | 102485229 A | 6/2012 |
| CN | 103845345 A | 6/2014 |
| CN | 103923124 A | 7/2014 |
| CN | 104072539 A | 10/2014 |
| CN | 104558035 A | 4/2015 |
| CN | 104628773 A | 5/2015 |
| EP | 00206459 A2 | 12/1986 |
| EP | 269947 A1 | 6/1988 |
| EP | 270885 A1 | 6/1988 |
| EP | 402646 A1 | 12/1990 |
| EP | 481214 A1 | 4/1992 |
| EP | 745893 A2 | 12/1996 |
| EP | 829493 A2 | 3/1998 |
| EP | 853084 A2 | 7/1998 |
| EP | 989122 A1 | 3/2000 |
| EP | 0996430 A2 | 5/2000 |
| EP | 1065207 A1 | 1/2001 |
| EP | 1627902 A1 | 2/2006 |
| JP | 2001031690 A | 2/2001 |
| JP | 2001031691 A | 2/2001 |
| KR | 2012025678 A | 3/2012 |
| WO | 9119721 A1 | 12/1991 |
| WO | 9209611 A1 | 6/1992 |
| WO | 9319075 A1 | 9/1993 |
| WO | 9403467 A2 | 2/1994 |
| WO | 9404143 A1 | 3/1994 |
| WO | 9418200 A1 | 8/1994 |
| WO | 9507920 A1 | 3/1995 |
| WO | 9623801 A2 | 8/1996 |
| WO | 9629336 A1 | 9/1996 |
| WO | 9633200 A1 | 10/1996 |
| WO | 9713507 A1 | 4/1997 |
| WO | 9717969 A1 | 5/1997 |
| WO | 9724361 A1 | 7/1997 |
| WO | 9735855 A1 | 10/1997 |
| WO | 9735990 A2 | 10/1997 |
| WO | 98004569 A1 | 2/1998 |
| WO | 9811121 A1 | 3/1998 |
| WO | 9842758 A1 | 10/1998 |
| WO | 1999/005150 A1 | 2/1999 |
| WO | 9941277 A1 | 8/1999 |
| WO | 9945016 A2 | 9/1999 |
| WO | 9962871 A1 | 12/1999 |
| WO | 2000014095 A1 | 3/2000 |
| WO | 2000018775 A1 | 4/2000 |
| WO | 2000038666 A2 | 7/2000 |
| WO | 2000075236 A1 | 12/2000 |
| WO | 2000076505 A1 | 12/2000 |
| WO | 2001032636 A1 | 5/2001 |
| WO | 2001049688 A1 | 7/2001 |
| WO | 2001066553 A2 | 9/2001 |
| WO | 2001098344 A2 | 12/2001 |
| WO | 0208241 A2 | 1/2002 |
| WO | 200204475 A1 | 1/2002 |
| WO | 2002003978 A2 | 1/2002 |
| WO | 2002008241 A2 | 1/2002 |
| WO | 2002012366 A1 | 2/2002 |
| WO | 2002020475 A2 | 3/2002 |
| WO | 2002022572 A2 | 3/2002 |
| WO | 2002094185 A2 | 11/2002 |
| WO | 2002096892 | 12/2002 |
| WO | 2003006628 | 1/2003 |
| WO | 2003016274 A2 | 2/2003 |
| WO | 2003020773 A2 | 3/2003 |
| WO | 2003024943 A2 | 3/2003 |
| WO | 03053989 A1 | 7/2003 |
| WO | 2003087298 A2 | 10/2003 |
| WO | 2003091264 A2 | 11/2003 |
| WO | 2003095665 | 11/2003 |
| WO | 2004024681 A2 | 3/2004 |
| WO | 2004029064 A1 | 4/2004 |
| WO | 2004037161 A2 | 5/2004 |
| WO | 2004041167 A2 | 5/2004 |
| WO | 2004064845 A1 | 8/2004 |
| WO | 2004096285 A2 | 11/2004 |
| WO | 2004101579 A2 | 11/2004 |
| WO | 2005012324 A2 | 2/2005 |
| WO | 2005016942 A1 | 2/2005 |
| WO | 2005044279 A1 | 5/2005 |
| WO | 2005044757 A1 | 5/2005 |
| WO | 2005058330 A1 | 6/2005 |
| WO | 2005066189 A1 | 7/2005 |
| WO | 2005079812 A1 | 9/2005 |
| WO | 2005085183 A1 | 9/2005 |
| WO | 2005087788 A2 | 9/2005 |
| WO | 2005123729 A1 | 12/2005 |
| WO | 2006013203 A2 | 2/2006 |
| WO | 2006017044 A2 | 2/2006 |
| WO | 2006059357 A2 | 6/2006 |
| WO | 2006102594 A1 | 9/2006 |
| WO | 2006114064 A2 | 11/2006 |
| WO | 2006114065 A2 | 11/2006 |
| WO | 2006114492 A1 | 11/2006 |
| WO | 2006130217 A2 | 12/2006 |
| WO | 2006133632 A1 | 12/2006 |
| WO | 2007002808 A1 | 1/2007 |

(56) References Cited

FOREIGN PATENT DOCUMENTS

| | | |
|---|---|---|
| WO | 2007002912 A2 | 1/2007 |
| WO | 2007009236 A1 | 1/2007 |
| WO | 2007013085 A1 | 2/2007 |
| WO | 2007013086 A1 | 2/2007 |
| WO | 2007014352 A2 | 2/2007 |
| WO | 2007044565 A2 | 4/2007 |
| WO | 2002057288 A1 | 5/2007 |
| WO | 2007084157 A2 | 7/2007 |
| WO | 2007/095269 A2 | 8/2007 |
| WO | 2007101371 A1 | 9/2007 |
| WO | 2007111994 A2 | 10/2007 |
| WO | 2007128815 A1 | 11/2007 |
| WO | 2007130783 A2 | 11/2007 |
| WO | 2007134457 A1 | 11/2007 |
| WO | 2007136650 A2 | 11/2007 |
| WO | 2007143823 A1 | 12/2007 |
| WO | 2007143824 A1 | 12/2007 |
| WO | 2008005555 A1 | 1/2008 |
| WO | 2008007392 A2 | 1/2008 |
| WO | 2008010985 A2 | 1/2008 |
| WO | 2008047345 A1 | 4/2008 |
| WO | 2008056264 A1 | 5/2008 |
| WO | 2008082601 A2 | 7/2008 |
| WO | 2008088147 A1 | 7/2008 |
| WO | 2008093173 A1 | 8/2008 |
| WO | 2008096369 A2 | 8/2008 |
| WO | 2008104408 A2 | 9/2008 |
| WO | 2008134578 A2 | 11/2008 |
| WO | 2008140302 A1 | 11/2008 |
| WO | 2008143500 A1 | 11/2008 |
| WO | 2008157657 A1 | 12/2008 |
| WO | 2009005693 A1 | 1/2009 |
| WO | 2009023718 A2 | 2/2009 |
| WO | 2009/052050 A1 | 4/2009 |
| WO | 2009046573 A1 | 4/2009 |
| WO | 2009055289 A2 | 4/2009 |
| WO | 2009064174 A1 | 5/2009 |
| WO | 2009074351 A2 | 6/2009 |
| WO | 2009077671 A1 | 6/2009 |
| WO | 2009094190 A2 | 7/2009 |
| WO | 2009105513 A1 | 8/2009 |
| WO | 2009130437 A1 | 10/2009 |
| WO | 2010026603 A2 | 3/2010 |
| WO | 2010068708 A2 | 6/2010 |
| WO | 2010081082 A2 | 7/2010 |
| WO | 2010091386 A2 | 8/2010 |
| WO | 2010108995 A1 | 9/2010 |
| WO | 2010125200 A1 | 11/2010 |
| WO | 2010142761 A1 | 12/2010 |
| WO | 2011005672 A2 | 1/2011 |
| WO | 2011017253 A1 | 2/2011 |
| WO | 2011031628 A1 | 3/2011 |
| WO | 2011038207 A1 | 3/2011 |
| WO | 2011053812 A1 | 5/2011 |
| WO | 2011069688 A1 | 6/2011 |
| WO | 2011100698 A2 | 8/2011 |
| WO | 2011111074 A2 | 9/2011 |
| WO | 2011128374 A1 | 10/2011 |
| WO | 2011130557 A1 | 10/2011 |
| WO | 2011133963 A2 | 10/2011 |
| WO | 2011150360 A1 | 12/2011 |
| WO | 2012079035 A1 | 6/2012 |
| WO | 2012098255 A1 | 7/2012 |
| WO | 2012116050 A2 | 8/2012 |
| WO | 2012117219 A1 | 9/2012 |
| WO | 2012142671 A1 | 10/2012 |
| WO | 2012149236 A1 | 11/2012 |
| WO | 2012149567 A1 | 11/2012 |
| WO | 2012154698 A2 | 11/2012 |
| WO | 2013019874 A1 | 2/2013 |
| WO | 2013052094 A2 | 4/2013 |
| WO | 2013078277 A1 | 5/2013 |
| WO | 2013078288 A1 | 5/2013 |
| WO | 2013090420 A2 | 6/2013 |
| WO | 2013095684 A1 | 6/2013 |
| WO | 2013115916 A1 | 8/2013 |
| WO | 2013116720 A1 | 8/2013 |
| WO | 2013116730 A1 | 8/2013 |
| WO | 2013167743 A1 | 11/2013 |
| WO | 2013175231 A1 | 11/2013 |
| WO | 2013187978 A1 | 12/2013 |
| WO | 2014032481 A1 | 3/2014 |
| WO | 2014033688 A1 | 3/2014 |
| WO | 2014068265 A1 | 5/2014 |
| WO | 2014070771 A1 | 5/2014 |
| WO | 2014088923 A1 | 6/2014 |
| WO | 2014099578 A1 | 6/2014 |
| WO | 2014177464 A2 | 11/2014 |
| WO | 2014183462 A1 | 11/2014 |
| WO | 2015040640 A2 | 3/2015 |
| WO | 2015079240 A1 | 6/2015 |
| WO | 2015079241 A1 | 6/2015 |

OTHER PUBLICATIONS

Lee, W., G. He, E. Eisenberg, T. Cihlar, S. Swaminathan, A. Mulato, and K. Cundy "Selective Intracellular Activation of a Novel Prodrug of the Human Immunodeficiency Virus Reverse Transcriptase Inhibitor Tenofovir leads to Preferential Distribution and Accumulation in Lymphatic Tissue" Antimicro. Agents Chemother. (2005), 49 (5), pp. 1898-1906.*

Birkus, G., N. Kutty, G. He, A. Mulato, W. Lee, M. McDermott, and T. Cihlar "Activation of 9-[(R)-2-[[(S)-[[(S)-1(Isopropoxycarbonyl)ethyl]amino]phenoxyphosphinyl]-methoxy]propyl]adenine (GS-7340) and Other Tenofovir Phosphonoamidate Prodrugs by Human Proteases" Mol. Pharmacol. (2008), 74(1), pp. 92-100.*

Int'l Search Report dated Oct. 17, 2013 in Int'l Application No. PCT/CN2013/079123.

Journal of Medicinal Chemistry (2011), 54(16), 5680-5693 (Tyrosine-based 1-(S)-[3-hydroxy-2-(phosphonomethoxy)propyl]cytosine and -adenine ((S)-HPMPC and (S)-HPMPA) prodrugs: Synthesis, stability, antiviral activity, and in vivo transport studies) (Abstract Only).

Nucleosides, Nucleotides & Nucleic Acids (2001), 20(4-7), 621-628 (Practical synthesis, separation, and stereochemical assignment of the PMPA pro-drug GS-7340) (Abstract Only).

Bioorganic & Medicinal Chemistry Letters (2001), 11(8), 1053-1056 (Synthesis and evaluation of novel amidate prodrugs of PMEA and PMPA) (Abstract Only).

International Journal of Antimicrobial Agents (1999), 12(1), 53-61 (Inhibition of the in vitro growth of Plasmodium falciparum by acyclic nucleoside phosphonates) (Abstract Only).

Drug Metabolism and Disposition (1997), 25(3), 362-366 (Pharmacokinetics and metabolism of selected prodrugs of PMEA in rats).

Nucleosides & Nucleotides (1995), 14(3-5), 767-70 (In vivo antiretroviral efficacy of oral bis(POM)-PMEA, the bis(pivaloyloxymethyl)prodrug of 9-(2-phosphonylmethoxyethyl)adenine (PMEA)) (Abstract Only).

Journal of Medicinal Chemistry (1994), 37(12), 1857-64 (Synthesis, Oral Bioavailability Determination, and in vitro Evaluation of Prodrugs of the Antiviral Agent 9-[2-(Phosphonomethoxy)ethyl]adenine (PMEA)) (Abstract Only).

Balzarini et al. Federation of European Biochemical Societies, 410 (1997) 324-328.

Perrone et al. J. Med. Chem. (2007) 50, 1840-1849.

Cahard et al. Mini-Reviews in Medicinal Chemistry (2004) 4, 371-381.

Pertusati et al. Antiviral Chem and Chemotherapy (2012) 22, 181-203.

* cited by examiner

TENOFOVIR PRODRUG AND PHARMACEUTICAL USES THEREOF

CROSS-REFERENCE TO RELATED APPLICATIONS

This application is a Section 371 of International Application No. PCT/CN2013/079123, filed on Jul. 10, 2013, which was published in the Chinese language on Mar. 6, 2014, under International Publication No. WO 2014/032481 A1, and the disclosure of which is incorporated herein by reference.

FIELD OF THE INVENTION

The present invention relates to a tenofovir prodrug and a stereoisomer, pharmaceutically acceptable salt, hydrate, or solvate thereof, as well as their medical use.

BACKGROUND OF THE INVENTION

Hepatitis B virus (HBV) is a kind of DNA virus that causes human acute or chronic hepatitis. As HBV infection is a direct cause of serious liver disease including cirrhosis and hepatocellular carcinoma in humans, hepatitis B is a major threat to human health. HBV-DNA (deoxyribonucleic acid) is the core of HBV and the basis of viral replication. Nucleotides can inhibit viral polymerases by competitive binding to the natural deoxyribose substrate directly, and terminate the DNA chain by inserting DNA. Thus, nucleotides, such as Cidofovir, Adefovir, Lamivudine, and Tenofovir, are the main drugs for treating hepatitis B. Tenofovir is a novel nucleotide reverse transcriptase inhibitor, which is effective against a variety of viruses for the treatment of viral infections. As the phosphate group is a dianion at physiological pH, tenofovir has poor cell membrane permeability, low bioavailability, and dose-dependent renal toxicity, which limits its therapeutic effect. Thus, tenofovir must be prepared into a phosphonate prodrug form via various technical means, such as esterification and salification, for clinical applications. For example, Tenofovir disoproxil fumarate developed by Gilead Sciences Inc. is the first generation oral active tenofovir prodrug for the treatment of HIV infection and hepatitis B.

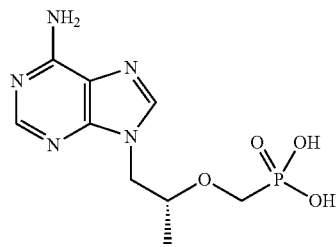

Tenofovir

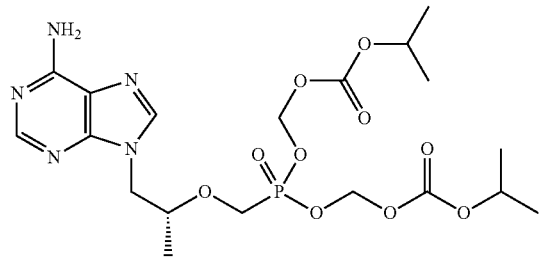

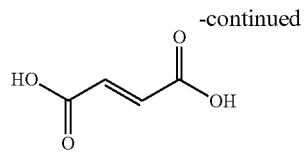

Tenofovir disoproxil fumarate

As Tenofovir disoproxil fumarate is highly sensitive to serum enzyme mediated hydrolysis reactions, its drug concentration cannot be effectively increased at the active site. Moreover, two equivalents of potentially toxic formaldehyde are released upon metabolism, and side effects such as lactic acidosis, severe hepatomegaly and lipodystrophy have been found during clinical use. In order to improve the stability of tenofovir prodrug in plasma and reduce the metabolite-tenofovir concentration to reduce drug toxicity, many pharmaceutical companies are conducting research and development on the next generation of tenofovir prodrugs, and have made some progress. Some new prodrugs have been in phase I/II clinical studies. For example, International Patent Application WO0208241 discloses a kind of natural amino acid (monosubstituted) synthesized tenofovir phosphonamidate prodrug (e.g., GS-7340), and International Patent Application WO2009105513 discloses a kind of novel tenofovir phosphate bisamide prodrug. Compared to tenofovir phosphodiester, these novel prodrugs have improved plasma stability, thereby increasing the cumulative concentration of the active metabolite-tenofovir in peripheral blood mononuclear cells (PBMCs) and the therapeutic effect. For example, the total concentration of the active ingredient produced by GS-7340 in PBMCs is 10 times greater than tenofovir disoproxil, and 30 times greater than tenofovir. However, GS-7340 has certain degradation in plasma and 1-2% of the metabolite-tenofovir can be detected in plasma. So it is inevitable that GS-7340 has toxicity as a side effect generated by tenofovir disoproxil, which results in drug safety problems. Thus, it is important to further develop a tenofovir prodrug with high efficacy and low toxicity. With the purpose of further improving the stability of tenofovir disoproxil in plasma, the present invention synthesizes a series of tenofovir phosphonamidate prodrugs with disubstituted amino acids. This kind of prodrug is proven to be very stable in plasma and no metabolite-tenofovir is found in plasma. On the other hand, the concentration of active metabolite-tenofovir in PBMCs is increased significantly compared with GS-7340. Thus, the present invention makes it possible to provide a new generation of tenofovir prodrugs with high efficacy and low toxicity.

SUMMARY OF THE INVENTION

Surprisingly, the inventors found a series of compounds, which have higher efficacy and lower toxicity than the prior art. Compared to GS-7340, the compounds according to the present invention are stable enough in plasma, and the metabolite-tenofovir is completely undetectable in plasma. On the other hand, the concentration of tenofovir is greatly improved in PBMCs. Such a result is totally unexpected for those skilled in the art.

The present invention relates to a compound of general formula (I) and a stereoisomer, pharmaceutically acceptable salt, hydrate, or solvate thereof:

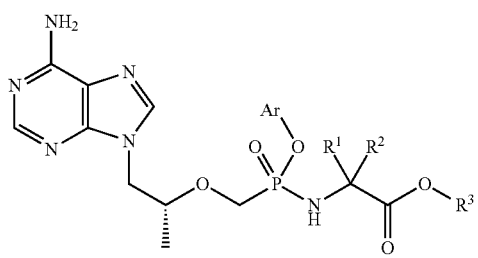

(I)

wherein:

R¹ and R² are $C_{1-6}$ alkyl respectively, or R¹ and R² together with the attached carbon atom form a $C_{3-7}$ cycloalkyl;

R³ is hydrogen, $C_{1-6}$ alkyl, substituted or unsubstituted $C_{6-10}$ aryl or 6- to 10-membered heteroaryl;

Ar is substituted or unsubstituted $C_{6-10}$ aryl or 6- to 10-membered heteroaryl.

The compound of general formula (I) according to the present invention can be used as a prodrug of tenofovir. This prodrug is stable in plasma and the concentration of active metabolite-tenofovir in PBMCs is improved significantly compared to that of GS-7340.

In the compound of general formula (I) according to the present invention, the phosphorus atom is chiral and the configuration is S or R, or a mixture of R and S.

In an embodiment of the present invention, the compound of general formula (I) or the stereoisomer, pharmaceutically acceptable salt, hydrate or solvate thereof, wherein the stereoisomer comprises a tautomer, cis-trans isomer, conformational isomer, mesomer or enantiomeric or diastereomeric optical isomer.

In a preferred embodiment of the present invention, compounds having the following structures are provided, but the compound of general formula (I) according to the present invention is not limited to the following structures:

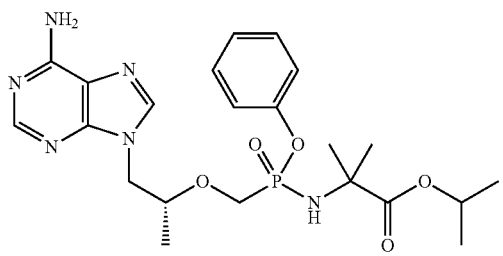

Ia

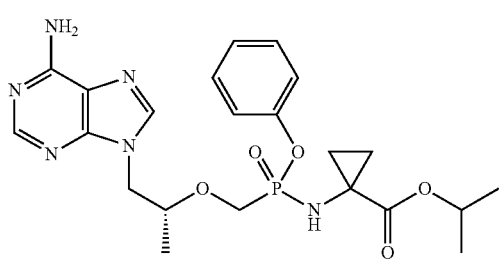

Ib

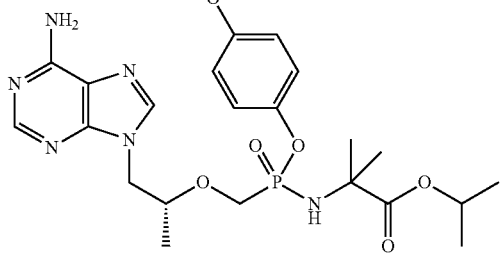

Ic

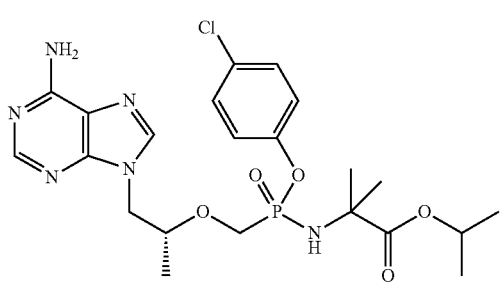

Id

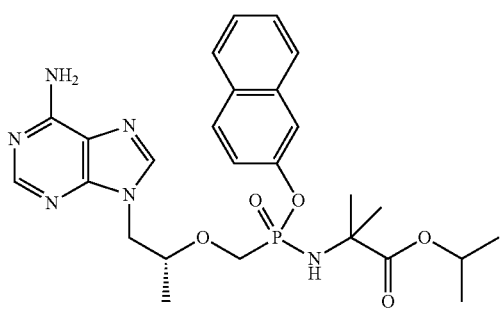

Ie

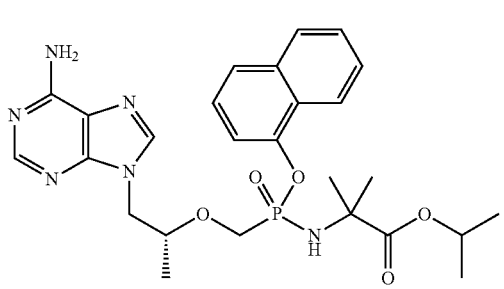

If

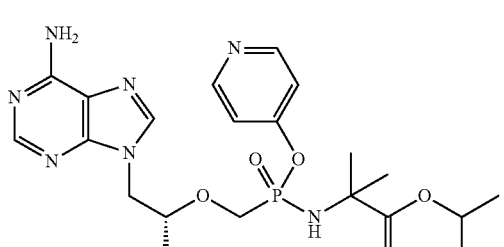

Ig

Ih
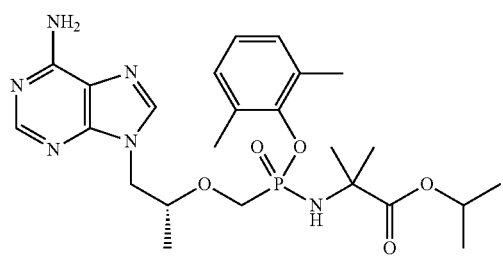
Ii
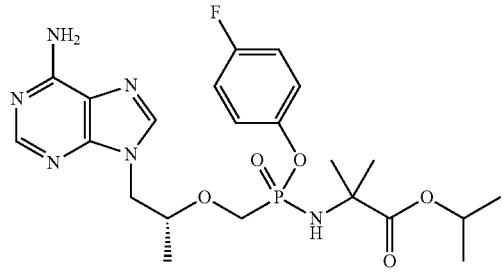
Ij
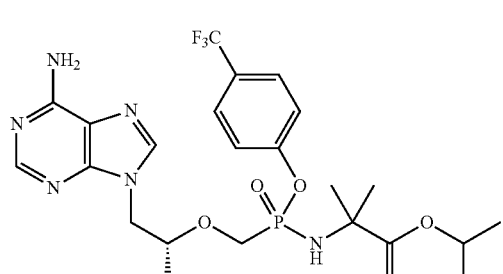
Ik
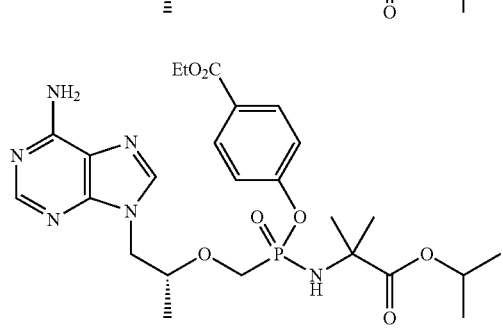
In another preferred embodiment of the present invention, chiral compounds with the following structures are disclosed, but the compound of general formula (I) according to the present invention is not limited to the following structures:
Ia1
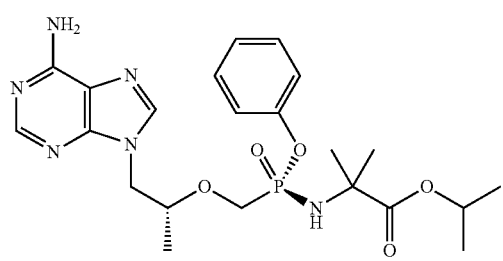
Ib1
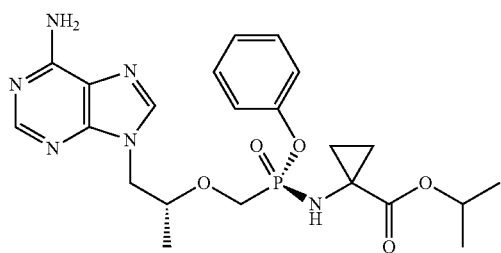
Ic1
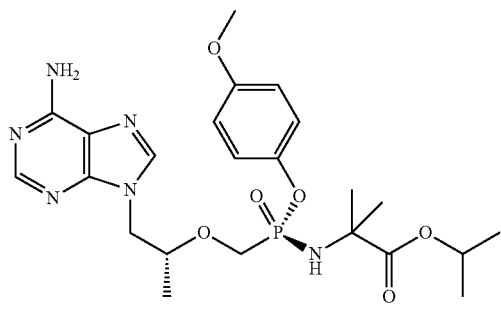
Id1
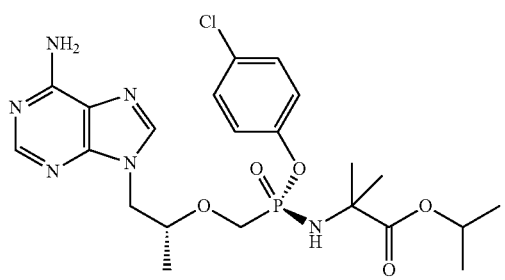
Ie1
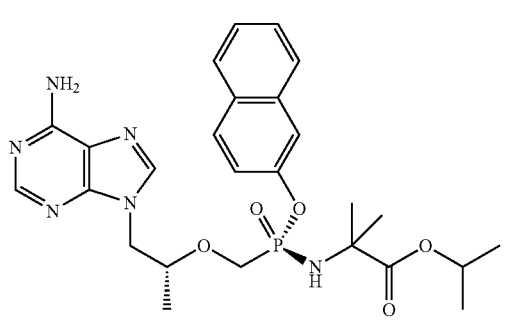
If1
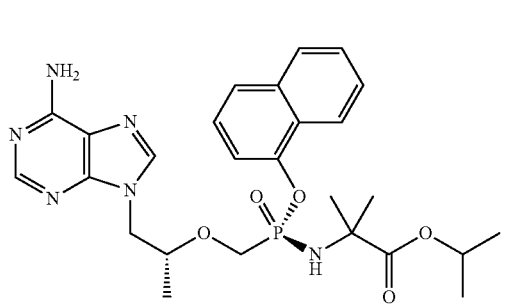

-continued

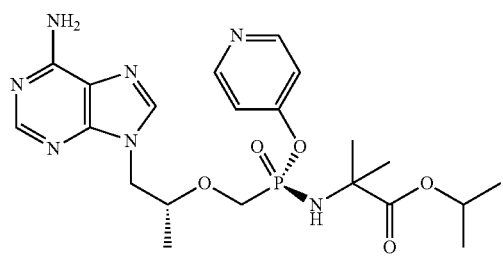
Ig1

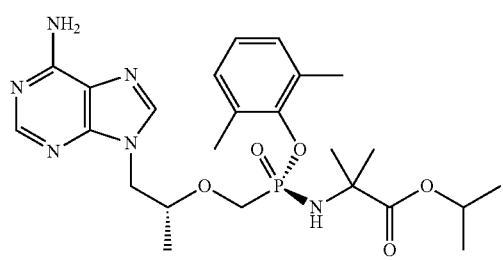
Ih1

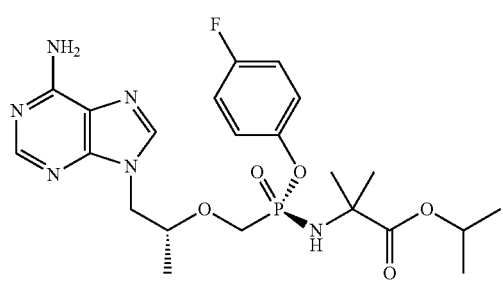
Ii1

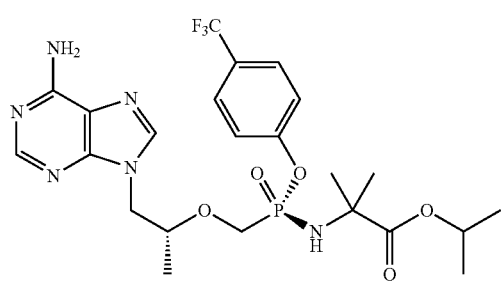
Ij1

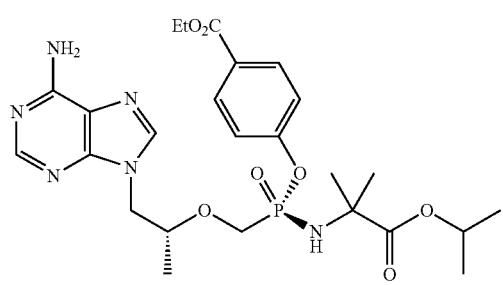
Ik1

The compound of general formula (I) according to the present invention can be prepared according to the following method:

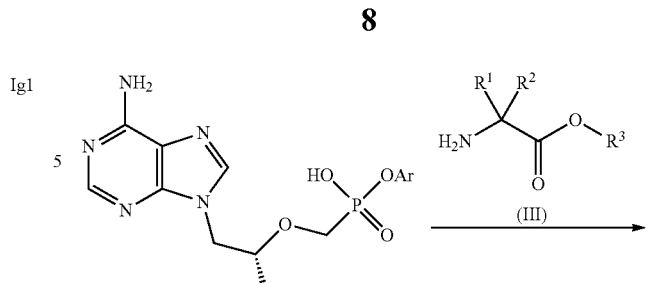
(II)

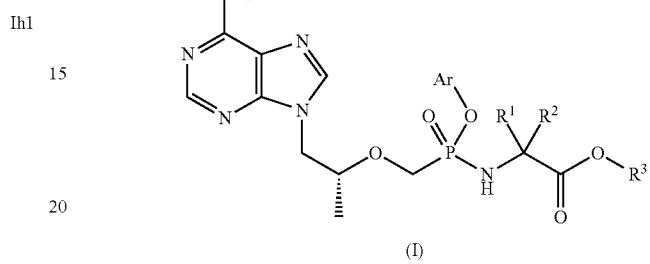
(I)

wherein the compound of general formula (II) can be prepared from tenofovir according to the method of Chinese Patent ZL01813161.1 as well as other conventional methods in the art.

Chiral isomer (I1) can be separated from a mixture of isomers (I') with a reverse phase column or chiral column.

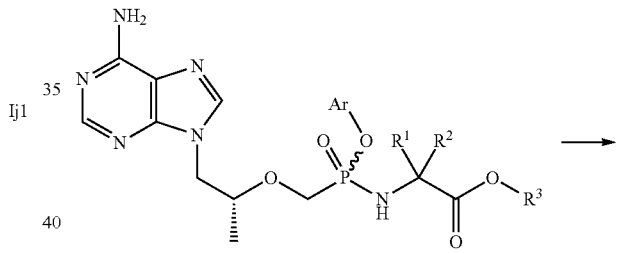
(I')

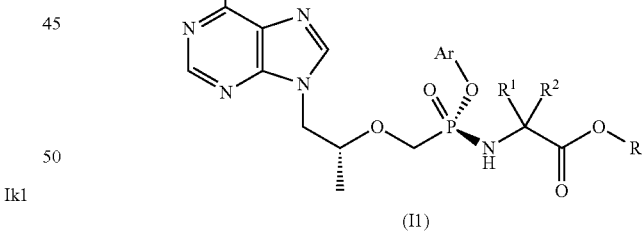
(I1)

The present invention also provides a pharmaceutical composition comprising a compound of general formula (I) or a stereoisomer, pharmaceutically acceptable salt, hydrate, or solvate thereof and a pharmaceutically acceptable carrier, wherein the pharmaceutically acceptable carrier is selected from the group consisting of water for injection, lyophilized powder excipient, and oral preparation excipient.

The present invention also relates to the use of a compound of general formula (I) or a stereoisomer, pharmaceutically acceptable salt, hydrate, or solvate thereof or the pharmaceutical composition in the preparation of a medicament for the treatment of viral infections, preferably hepatitis B or diseases caused by hepatitis B virus.

Unless otherwise stated, the terms in the present invention have the following meanings.

The term "alkyl" means saturated aliphatic hydrocarbon groups comprising a straight or branched chain having 1 to 6 carbon atoms. Examples of alkyl include, but are not limited to, methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. Alkyl can be substituted or unsubstituted. When substituted, the substituent can be substituted at any possible attachment point, and the substituent is preferably one or more groups independently selected from the group consisting of alkyl, alkenyl, alkynyl, alkoxy, alkylthio, alkylamino, halogen, thiol, hydroxyl, nitro, cyano, cycloalkyl, heterocycloalkyl, aryl, heteroaryl, cycloalkoxy, heterocycloalkoxy, cycloalkylthio, heterocycloalkylthio, and oxo.

The term "cycloalkyl" means a saturated or partially unsaturated monocycle or polycycle hydrocarbon substituent, which comprises 3 to 7 carbon atoms. Examples of monocyclic cycloalkyl include, but are not limited to, cyclopropyl, cyclobutyl, cyclopentyl, cyclopentenyl, cyclohexyl, cyclohexenyl, cyclohexadienyl, cycloheptyl, cycloheptatrienyl and the like. Examples of polycyclic cycloalkyl include, but are not limited to, spiro-ring cycloalkyl, fused-ring cycloalkyl and bridged-ring cycloalkyl. The cycloalkyl can be substituted or unsubstituted. When substituted, the substituent is preferably one or more groups independently selected from the group consisting of alkyl, alkoxy, halogen, hydroxy, nitro, cyano, cycloalkyl, heterocycloalkyl, aryl, and heteroaryl.

The term "aryl" means a 6 to 10 membered full-carbon monocycle or fused polycycle (i.e., rings which share adjacent pairs of carbon atoms) and polycycle having a conjugated π electron system (i.e., rings having adjacent pairs of carbon atoms), such as phenyl and naphthyl. The aryl can be substituted or unsubstituted. When substituted, the substituent is preferably one or more groups independently selected from the group consisting of alkyl, alkenyl, alkynyl, alkoxy, alkylthio, alkylamino, halogen, thiol, hydroxyl, nitro, cyano, cycloalkyl, heterocycloalkyl, aryl, heteroaryl, cycloalkoxy, heterocycloalkoxy, cycloalkylthio, and heterocycloalkylthio.

The term "heteroaryl" means a heteroaromatic system of 6 to 10 ring atoms, preferably 5 to 6 ring atoms, which comprises one, two, three or four heteroatoms including O, S or N, such as pyridinyl, or pyrimidinyl. "Heteroaryl" can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxyl, nitro, cyano, cycloalkyl, heterocycloalkyl, aryl, heteroaryl, cycloalkoxyl, heterocycloalkoxy, cycloalkylthio, and heterocycloalkylthio.

DETAILED DESCRIPTION OF THE INVENTION

The present invention will be illustrated by the following examples which enable those skilled in the art to understand the present invention more clearly. The examples are merely for illustrating the technical solutions of the present invention and should not be considered as limiting the scope of the invention.

Example 1

Step 1:

Trimethylchlorosilane (6.0 g) was added dropwise to a solution of phenol (5 g) and triethylamine (10.1 mL) in dichloromethane (150 mL) at 0° C. After addition, the reaction mixture was stirred for 18 hours after the temperature was raised to 20° C. The white solid was removed and washed with dichloromethane. The filtrate was combined and the solvent was evaporated to give phenoxy trimethylsilane (4.2 g) as a colorless oil.

Step 2:

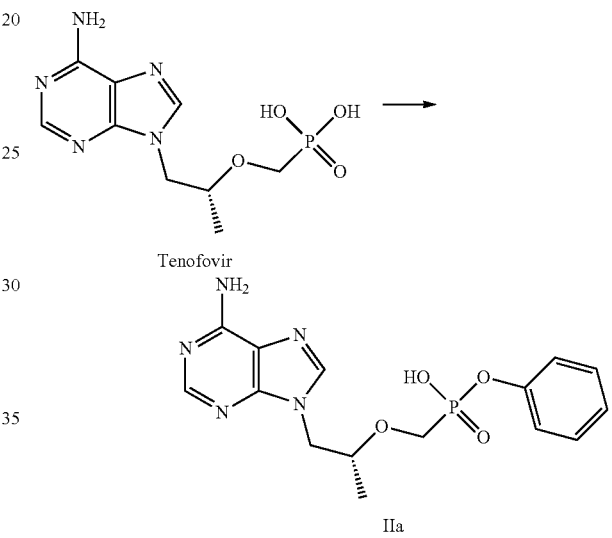

DMF (0.1 mL) and dichlorosulfoxide (0.73 g) were added to a suspension of tenofovir (1 g, purchased from Suzhou Henderson Pharmaceutical Co., Ltd.) in sulfolane (2.5 mL) at 70° C., and then the temperature was raised to 100° C. The reaction mixture was stirred at 100° C. for 1.5 hours until a clear solution was obtained. Then, phenoxy trimethylsilane (0.70 g) was added rapidly, and the mixture was left to stir at 100° C. for another 1.5 hours. Then, the solvent was evaporated to give a viscous yellow oil. The oil was dissolved in methanol and adjusted to pH 3 with 45% aqueous potassium hydroxide. The precipitate was filtered and dried to give a white powder solid IIa (0.7 g). MS (m/z) 363.96 (MH+).

Step 3:

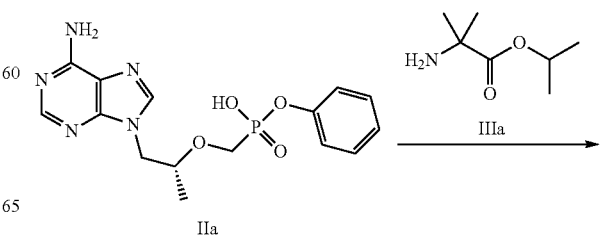

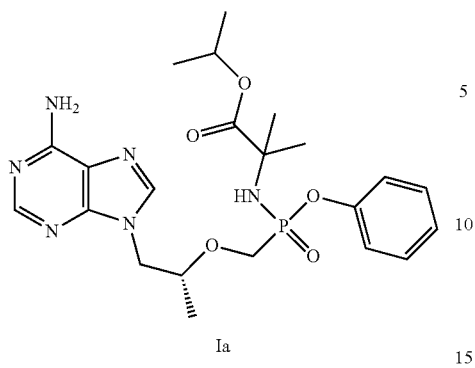

Ia

DMF (0.1 mL) and dichlorosulfoxide (343 mg) were added to a mixture of compound IIa (600 mg) in sulfolane (1 mL) at 60° C. The mixture was then stirred at 60° C. for 30 minutes until a clear solution was obtained. The resulting solution was added to a solution of amino acid ester IIIa (750 mg, purchased from Shanghai Darui Fine Chemicals Co., Ltd.) and diisopropylamine (452 mg) in dichloromethane (7 mL) at 0° C. The mixture was stirred at 20° C. for 2 hour, and then washed with 5% aqueous sodium dihydrogen phosphate and saturated brine, and dried over anhydrous sodium sulfate. The solvent was evaporated to give a yellow oil crude product, which was purified via column chromatography to give an oil product Ia (150 mg).

$^1$H-NMR (400 MHz, CDCl$_3$) δ 8.34 (m, 1H), 8.05 (m, 1H), 7.36~6.95 (m, 5H), 6.49 (b, 2H), 6.22~5.84 (m, 1H), 5.01 (m, 1H), 4.42 (m, 1H), 4.40~3.60 (m, 3H), 1.52~1.18 (m, 15H). MS (m/z) 491.13 (MH$^+$).

The Preparation of Chiral Compounds Ia1 and Ia2:

Method 1: Non-Chiral Column Preparation

The crude product Ia (150 mg) was separated via preparative HPLC (preparative column: Waters Symmetry C18, Mobile phase: A: 0.02% aqueous phosphoric acid; B: methanol) to give compound Ia1 (50 mg, retention time: 50.65 min): MS (m/z) 491.17 (MH$^+$) and compound Ia2 (61 mg, retention time: 47.57 min): MS (m/z) 491.10 (MH+).

Method 2: Chiral Column Preparation

The crude product Ia (150 mg) was separated via preparative HPLC (preparative column: Chiralpak AS-H, mobile phase: A: n-hexane; B: ethanol) to give compound Ia1 (62 mg, retention time: 6.53 min) and compound Ia2 (78 mg, retention time: 6.11 min).

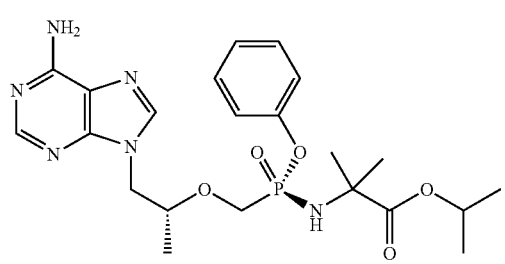

Ia1

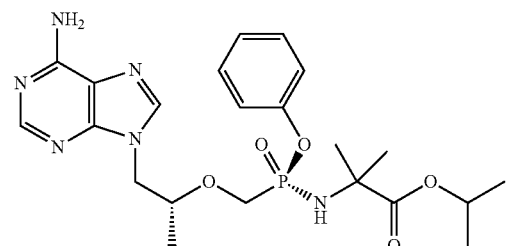

Ia2

Example 2

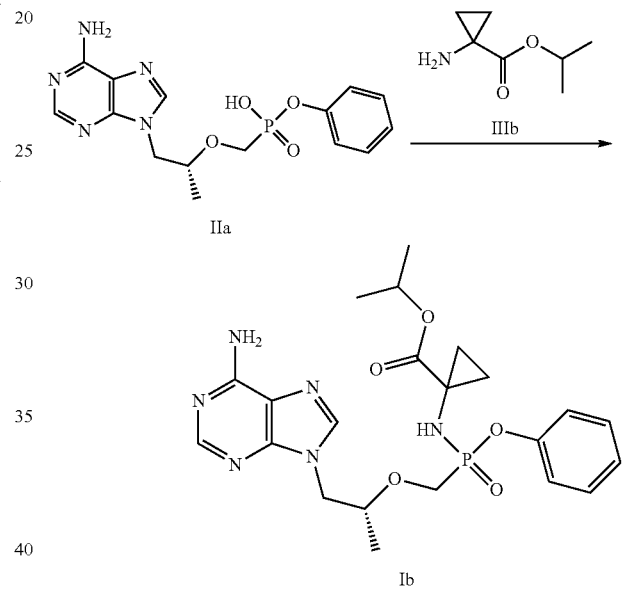

DMF (0.1 mL) and dichlorosulfoxide (343 mg) were added to a mixture of compound IIa (600 mg) in sulfolane (1 mL) at 60° C. The mixture was then stirred at 60° C. for 30 minutes until a clear solution was obtained. The resulting solution was added to a solution of amino acid ester IIIb (760 mg, purchased from Shanghai Darui Fine Chemicals Co., Ltd.) and diisopropylamine (452 mg) in dichloromethane (7 mL) at 0° C. The mixture was stirred at 20° C. for 2 hour, and then washed with 5% aqueous sodium dihydrogen phosphate and saturated brine, and dried over anhydrous sodium sulfate. The solvent was evaporated to give a yellow oil crude product, which was purified via column chromatography to give an oil product Ib (221 mg).

$^1$H-NMR (400 MHz, CDCl$_3$) δ 8.38 (m, 1H), 8.01 (m, 1H), 7.34~6.95 (m, 5H), 6.48~6.18 (m, 1H), 5.84 (b, 2H), 5.01~4.82 (m, 1H), 4.42 (m, 1H), 4.2~03.60 (m, 5H), 2.68 (m, 1H), 1.41~1.10 (m, 12H).

The crude product Ib (100 mg) was separated via preparative HPLC (preparative column: Chiralpak AS-H, mobile phase: A: n-hexane; B: ethanol) to give compound Ib1 (35 mg). MS (m/z) 489.26 (MH$^+$).

13

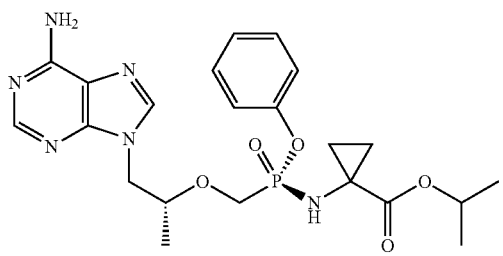

Example 3

Step 1:

Trimethylchlorosilane (6.3 g) was added dropwise to a solution of p-chlorophenol (5 g) and triethylamine (10.8 mL) in dichloromethane (150 mL) at 0° C. After addition, the reaction mixture was stirred for 18 hours after the temperature was raised to 20° C. The solvent was evaporated to give p-chlorophenoxy trimethylsilane (5.1 g) as a colorless oil.

Step 2:

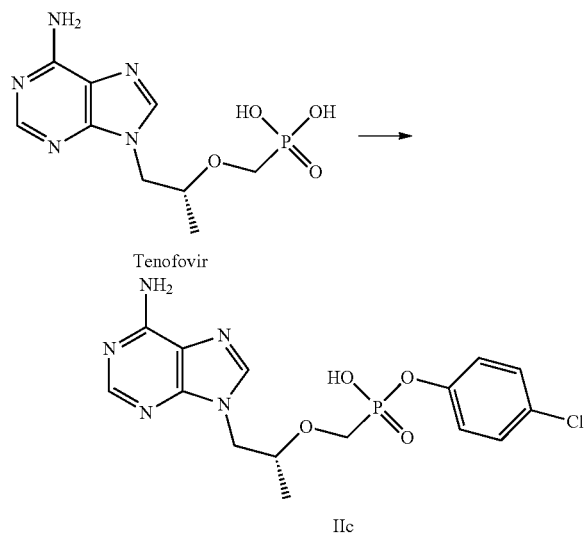

DMF (0.1 mL) and dichlorosulfoxide (0.73 g) were added to a suspension of tenofovir (1 g) in sulfolane (2.5 mL) at 70° C., and then the temperature was raised to 100° C. The reaction mixture was stirred at 100° C. for 1.5 hours until a clear solution was obtained. Then, p-chlorophenoxy trimethylsilane (0.77 g) was added rapidly, and the mixture was left to stir at 100° C. for 1.5 hours. The solvent was evaporated to give a viscous yellow oil. The oil was dissolved in methanol and then adjusted to pH 3 with 45% aqueous potassium hydroxide. The precipitate was filtered and dried to give a white powder solid IIc (800 mg). MS (m/z) 398.05 (MH+).

14

Step 3:

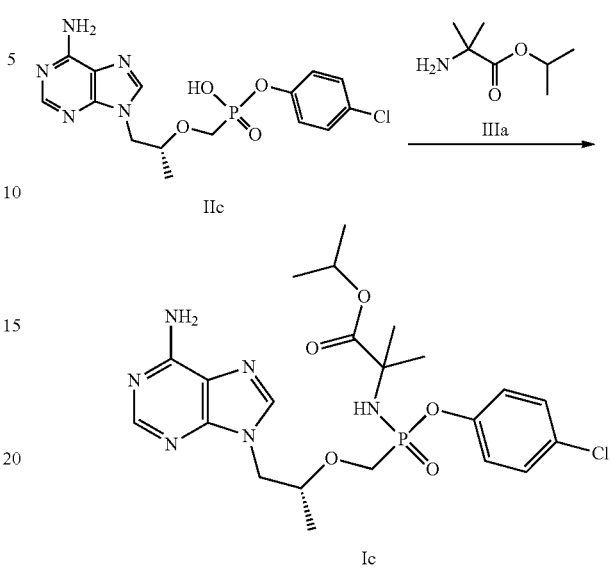

DMF (0.1 mL) and dichlorosulfoxide (343 mg) were added to a mixture of compound IIc (600 mg) in sulfolane (1 mL) at 60° C. The mixture was then stirred at 60° C. for 30 minutes until a clear solution was obtained. The resulting solution was added to a solution of amino acid ester IIIa (731 mg) and diisopropylamine (452 mg) in dichloromethane (7 mL) at 0° C. The mixture was stirred at 20° C. for 2 hours, and then washed with 5% aqueous sodium dihydrogen phosphate and saturated brine, and dried over anhydrous sodium sulfate. The solvent was evaporated to give a yellow oil crude product which was purified via column chromatography to give an oil product Ic (121 mg).

$^1$H-NMR (400 MHz, CDCl$_3$) δ 8.35 (m, 1H), 8.01 (m, 1H), 7.28 (m, 1H), 7.22 (m, 1H), 7.15~7.13 (m, 1H), 6.94 (m, 1H), 5.88 (b, 2H), 5.07 (m, 2H), 4.42 (m, 1H), 4.21 (m, 1H), 3.90~3.81 (m, 2H), 3.71~3.54 (m, 1H), 1.56~1.24 (m, 15H).

The crude product Ic (70 mg) was separated by preparative HPLC (preparative column: Chiralpak AS-H, mobile phase: A: n-hexane; B: ethanol) to give compound Ic1 (21 mg). MS (m/z) 525.26 (MH+).

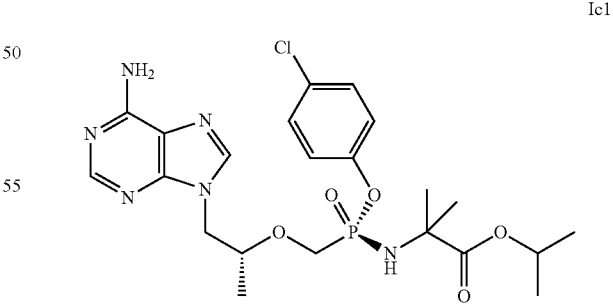

Example 4

Step 1:

Trimethylchlorosilane (6.3 g) was added dropwise to a solution of p-methoxyphenol (5 g) and triethylamine (10.8 mL) in dichloromethane (150 mL) at 0° C. After addition, the reaction mixture was stirred for 18 hours after the temperature was raised to 20° C. The solvent was evaporated to give p-methoxyphenoxy trimethylsilane (4.7 g) as a colorless oil.

Step 2:

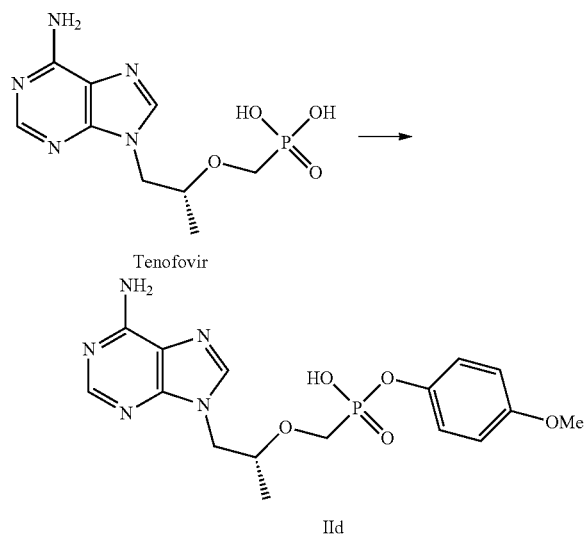

Tenofovir

IId

DMF (0.1 mL) and dichlorosulfoxide (0.73 g) were added to a suspension of tenofovir (1 g) in sulfolane (2.5 mL) at 70° C., and then the temperature was raised to 100° C. The reaction mixture was stirred at 100° C. for 1.5 hours until a clear solution was obtained. Then, p-methoxyphenoxy trimethylsilane (0.75 g) was added rapidly and the mixture was left to stir at 100° C. for 1.5 hours. The solvent was evaporated to give a viscous yellow oil. The oil was dissolved in methanol and then adjusted to pH 3 with 45% aqueous potassium hydroxide. The precipitate was filtered and dried to give a white powder solid IId (600 mg). MS (m/z) 394.11 (MH$^+$).

Step 3:

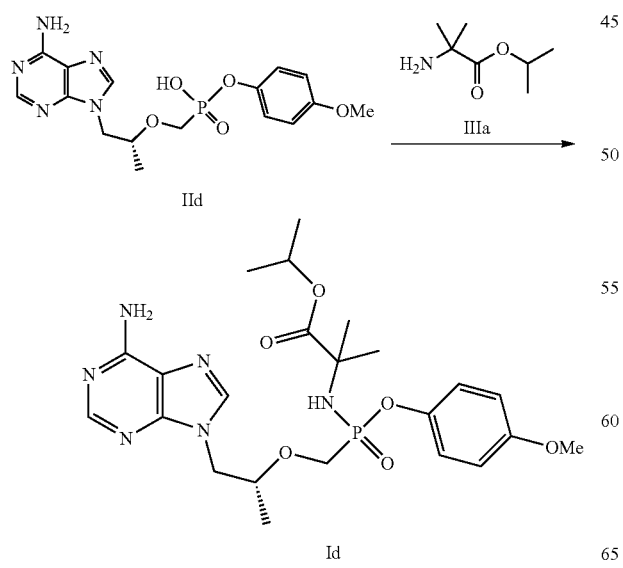

Id

DMF (0.1 mL) and dichlorosulfoxide (181 mg, 1.52 mmol) were added to a mixture of compound IId (300 mg) in sulfolane (1 mL) at 60° C. The mixture was then stirred at 60° C. for 30 minutes until a clear solution was obtained. The resulting solution was added to a solution of amino acid ester IIIa (386 mg) and diisopropylamine (343 mg) in dichloromethane (5 mL) at 0° C. The mixture was stirred at 20° C. for 2 hours, and then washed with 5% aqueous sodium dihydrogen phosphate and saturated brine, and dried over anhydrous sodium sulfate. The solvent was evaporated to give a yellow oil crude product, and then purified via column chromatography to give an oil product Id (40 mg). $^1$H-NMR (400 MHz, CDCl$_3$) δ 8.35 (m, 1H), 8.04 (m, 1H), 7.12~6.85 (m, 4H), 5.86 (b, 2H), 5.06 (m, 1H), 4.42 (m, 1H), 4.18 (m, 1H), 4.08~3.94 (m, 3H), 3.82 (m, 3H), 3.7~73.61 (m, 1H), 1.55~1.17 (m, 15H).

The crude product Id (30 mg) was separated by preparative HPLC (preparative column: Chiralpak AS-H, mobile phase: A: n-hexane; B: ethanol) to give 12 mg compound Id1. MS (m/z) 521.23 (MH$^+$).

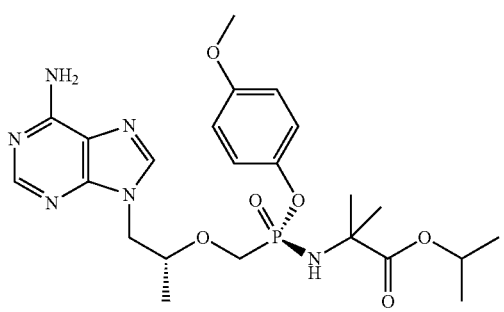

Id1

Example 5

Compounds Ie and Ie1 were prepared according to the same preparation method as that of compounds Ic and Ic1.

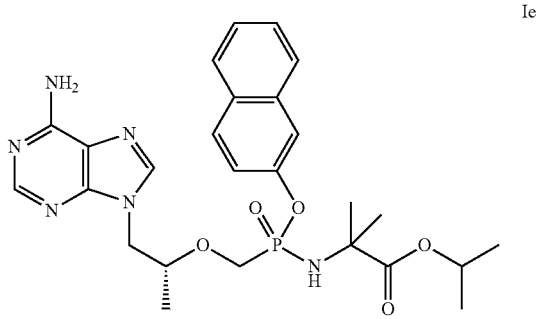

Ie

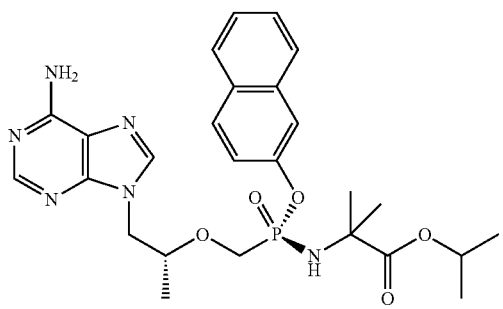

Ie: ¹H-NMR (400 MHz, CDCl₃) δ 8.27 (m, 1H), 8.04 (s, 1H), 7.96 (m, 1H), 7.84 (m, 1H), 7.62 (m, 1H), 7.52~7.33 (m, 4H), 5.78 (b, 2H), 5.04~4.98 (m, 1H), 4.38~3.71 (m, 6H), 1.57~1.06 (m, 15H).

Ie1: MS (m/z) 541.11.

Example 6

Compounds If and If1 were prepared according to the same preparation method as that of compounds Ic and Ic1.

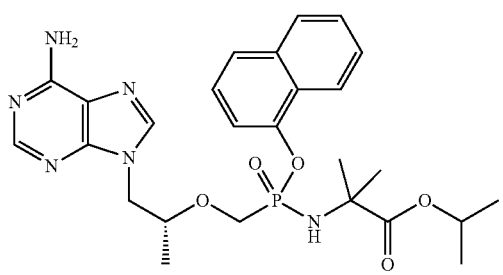

If: ¹H-NMR (400 MHz, CDCl₃) δ 8.33 (m, 1H), 8.02 (s, 1H), 7.81~7.66 (m, 4H), 7.49~7.41 (m, 2H), 7.31~7.06 (m, 1H), 5.72 (b, 2H), 5.06~4.99 (m, 1H), 4.43~4.35 (m, 1H), 4.19~3.91 (m, 4H), 3.74~3.65 (m, 1H), 1.57~1.20 (m, 15H).

If1: MS (m/z) 541.10.

Example 7

Compounds Ih and Ih1 were prepared according to the same preparation method as that of compounds Ic and Ic1.

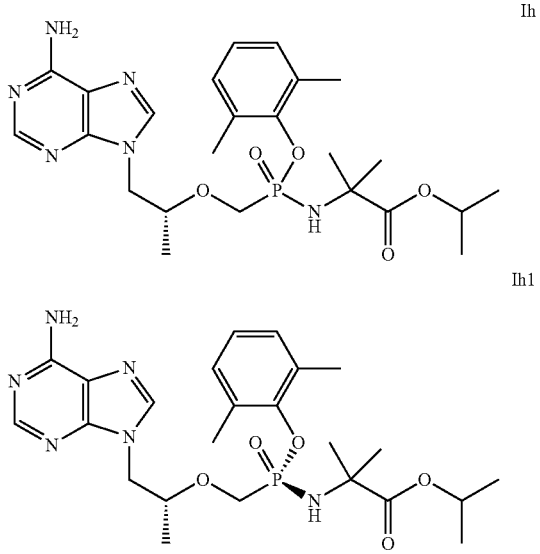

Ih: ¹H-NMR (400 MHz, CDCl₃) δ 8.33 (m, 1H), 7.95 (m, 1H), 7.00~6.95 (m, 3H), 5.83 (b, 2H), 5.05~4.99 (m, 2H), 4.35~4.31 (m, 1H), 4.23~4.17 (m, 1H), 4.01~3.83 (m, 3H), 3.80~3.77 (m, 1H), 2.35 (s, 3H), 2.31 (s, 3H), 1.33~1.19 (m, 15H).

Ih1: MS (m/z) 519.15.

Example 8

Compounds Ii and Ii1 were prepared according to the same preparation method as that of compounds Ic and Ic1.

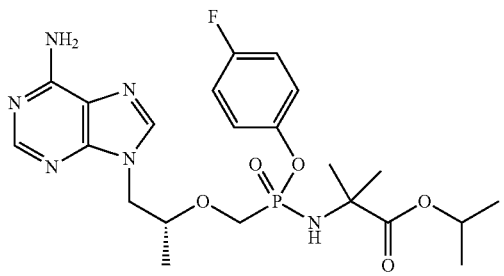

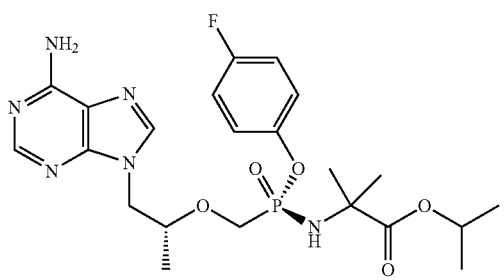

Ii: ¹H-NMR (400 MHz, CDCl₃) δ 8.36 (m, 1H), 8.00 (m, 1H), 7.17 (m, 1H), 7.02 (m, 1H), 6.97 (m, 2H), 5.71 (b, 2H), 5.06 (m, 1H), 4.43 (m, 1H), 4.20 (m, 1H), 4.06~3.84 (m, 3H), 3.72~3.61 (m, 1H), 1.56~1.22 (m, 15H).

Ii1: MS (m/z) 509.25.

Example 9

Compounds Ij and Ij1 were prepared according to the same preparation method as that of compounds Ic and Ic1.

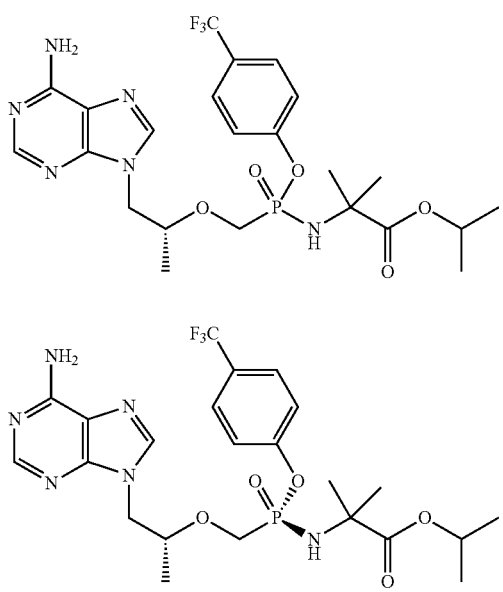

Ij: $^1$H-NMR (400 MHz, CDCl$_3$) δ 8.32 (m, 1H), 8.06 (s, 1H), 7.58 (m, 2H), 7.52 (m, 2H), 5.89 (b, 2H), 5.02~4.96 (m, 1H), 4.43~4.36 (m, 2H), 4.04~3.91 (m, 4H), 1.58~1.23 (m, 15H).

Ij1: MS (m/z) 559.08.

Example 10 Preparation of Fumarate of Compound Ia1

Compound Ia1 (480 mg), fumaric acid (120 mg) and acetonitrile were added sequentially to a single-necked flask at 20° C. The mixture was warmed to 60° C. and stirred at this temperature until the solid was completely dissolved. Stirring was continued for another 5 minutes, and then the solution was cooled to 20° C. and filtered to obtain the fumarate of compound Ia1 as a white granular solid (490 mg).

$^1$H NMR (400 MHz, D$_2$O) δ 7.21 (m, 2H), 7.11 (m, 1H), 6.67 (m, 2H), 6.57 (s, 2H), 4.77 (m, 1H), 4.29 (m, 1H), 4.17 (m, 1H), 4.06 (m, 1H), 3.93 (m, 1H), 1.07 (m, 6H), 1.21 (m, 9H).

Example 11 Antiviral Experiment

1. Study of In Vitro Anti-Hepatitis B Virus Activity

HepG 2.2.15 cell was used as the hepatitis B virus (HBV) vehicle to determine the inhibition effect of the compounds on DNA-replication of HBV.

Test method: HepG 2.2.15 cells were seeded into a 96-well culture plate. Various dilutions of test samples and positive control were added, respectively, after 24 hours, in which a cell control well was set. The medium was replaced with culture containing various dilutions of test samples after 72 hours. The supernatants and HepG 2.2.15 cells were collected after 6 days of culture. The HBV DNA-replication was tested via the dot blot method, and IC$_{50}$ was calculated (the results are shown in Table 1).

2. Cytotoxicity Test

Test method: HepG 2.2.15 cells were seeded into a 96-well culture plate and various dilutions of test samples and positive control were added, respectively. CellTiter-Blue (Promega, Catalog #G8081) was added for 6 days of culture. Fluorescence reading was counted with Flexstation 3 to calculate CC$_{50}$ (the results were shown in Table 1).

TABLE 1

HBV inhibition rate and cytotoxicity results of the compounds

| Compound | IC$_{50}$(nM) | Toxicity CC$_{50}$(nM) |
| --- | --- | --- |
| Positive control GS-7171(Mixture) | 35 | >10000 |
| Positive control GS-7340 (Chiral) | 14 | >10000 |
| Ia (Mixture) | 21 | >10000 |
| Ia1 (Chiral) | 5.0 | >10000 |
| Ia2 (Chiral) | 32 | >10000 |
| Ib1 (Chiral) | 15 | >10000 |
| Ic1 (Chiral) | 5.3 | >10000 |
| Id1 (Chiral) | 6.2 | >10000 |
| Ie1 (Chiral) | 5.7 | >10000 |
| If1 (Chiral) | 7.5 | >10000 |
| Ih1 (Chiral) | 5.9 | >10000 |
| Ii1 (Chiral) | 8.3 | >10000 |
| Ij1 (Chiral) | 7.0 | >10000 |

Positive control is GS-7171 and GS-7340, which are disclosed in Examples 2 and 3 of Chinese Patent ZL01813161.1. GS-7171 can be resolved into diastereomers GS-7340 and GS-7339, in which GS7340 has the better efficacy.

3. Conclusion

Experimental results show that the compounds Ia1, Ib1, Ic1, Id1, Ie1, If1, Ih1, and Ij1 have a significant inhibitory effect on HBV-DNA replication without cytotoxicity, in which the inhibitory effects on HBV-DNA replication of compounds Ia1, Ic1, Id1, Ie1, If1, Ih1, Ii1 and Ij1 were better than that of the positive control GS7340.

Example 12 Stability Test in Acidic Medium and Simulated Gastric Juice

1. Materials, Reagents and Manufacturers

| Name | Content | Manufacturer |
| --- | --- | --- |
| Pepsin | 1:3000 | Shanghai Runjie Chemical Reagent Co., Ltd. |
| HCl | 36% | Jiangsu Qiangsheng Chemical Co., Ltd. |
| Ammonium acetate | 98.0% | Sinopharm Chemical Reagent Co., Ltd. |
| GS-7340 | 98.7% | UniTris Biopharma Co. Ltd. |
| Ia1 | 98.7% | UniTris Biopharma Co. Ltd. |

2. Preparation of Reagents 2.1 Hydrochloric Acid Solution (pH 2.0)

4.5 mL of 36% hydrochloric acid was transferred into a 1 L volumetric flask and diluted with water to 1 L to prepare a stock solution. Then 10 mL of the above solution was transferred into a 50 mL volumetric flask and diluted with water to 50 mL to prepare the hydrochloric acid solution with pH 2.0.

2.2 Simulated Gastric Juice (pH 2.0)

10 ml of the stock solution and 500.0 mg of pepsin were transferred into a 50 mL volumetric flask and diluted with water to 50 ml, which was then subjected to ultrasound to dissolve the pepsin (the solution was not clear now) and then filtered to give a clear solution as simulated gastric juice.

2.3 Preparation of the Sample Solution
2.3.1 Hydrochloric Acid Solution of GS-7340
5.0 mg of GS-7340 were transferred into a 5 mL volumetric flask and mixed with 2.5 mL of isopropyl alcohol to dissolve GS-7340, and then the hydrochloric acid solution (pH 2.0) was added to 5 mL. The solution was shaken well and filtered for using.
2.3.2 Simulated Gastric Juice of GS-7340
5.0 mg of GS-7340 were transferred into a 5 mL volumetric flask and mixed with 2.5 mL of isopropyl alcohol to dissolve GS-7340, and then the simulated gastric juice was added to 5 mL. The solution was shaken well and filtered for using.
2.3.3 Hydrochloric Acid Solution of Compound Ia1
5.0 mg of compound Ia1 were transferred into a 5 mL volumetric flask and mixed with 2.5 mL of isopropyl alcohol to dissolve compound Ia1, and then the hydrochloric acid solution (pH 2.0) was added to 5 mL. The solution was shaken well and filtered for using.
2.3.4 Simulated Gastric Juice of Compound Ia1
5.0 mg of compound Ia1 were transferred into a 5 mL volumetric flask and mixed with 2.5 mL of isopropyl alcohol to dissolve compound Ia1, and then the simulated gastric juice was added to 5 mL. The solution was shaken well and filtered for using.
2.4 Sampling
The prepared sample was filled into the chromatography vial as the initial sample and immediately injected. Meanwhile, the rest of the samples were put into a 37° C. incubator, and were injected into the HPLC system after 6 hours.

The stability results of compound Ia1 and GS-7340 in an acid medium and simulated gastric juice are shown in Table 2.

TABLE 2

The stability results of compound Ia1 and GS-7340 in an acid medium and simulated gastric juice

| Sample | Acid medium (pH = 2) | | | Simulated gastric juice | | |
| --- | --- | --- | --- | --- | --- | --- |
| | Initial purity | Purity after 6 hours | Change value | Initial purity | Purity after 6 hours | Change value |
| GS-7340 | 98.7% | 95.5% | 3.2% | 98.7% | 94.4% | 4.3% |
| Ia1 | 98.7% | 98.1% | 0.6% | 98.7% | 98.2% | 0.5% |

3. Conclusion
Experimental results show that the stability of tenofovir phosphonamidate prodrug (Ia1) having a disubstituted amino acid is significantly improved compared to tenofovir phosphonamidate prodrug (GS-7340) having a monosubstituted amino acid.

Example 13: Metabolic Stability in Fresh Human Whole Blood and Distribution Test in PBMCs of Tenofovir Prodrug 1. Materials
Compound: Ia1 and GS-7340
2. Test Method
Different tenofovir prodrugs were incubated together with fresh human whole blood at 37° C. Plasma and PBMCs were separated, respectively, from the whole blood (Ficoll density gradient centrifugation method) after 1 hour and 2 hours incubation to determine the concentrations of prototype drug and metabolite-tenofovir in plasma and PBMCs. The PBMCs were counted via cell counter and each PBMC was treated as 200 fL to calculate intracellular drug concentration.
3. Plasma/PBMC Sample Treatment
20 μL of internal standard solution (400 ng/mL SN-38 solution), 5.04, methanol-water (50:50, v/v), and 200 μL acetonitrile were added to 100 μL plasma sample or PBMC sample, respectively. The mixture was mixed by vortex for 1 min and centrifuged for 5 min (14000 rpm). 20 μL supernatant and 180 μl mobile phase were mixed by vortex for 1 min, and 10 μL of the above mixture was injected into LC/MS/MS for analysis.

The results of the metabolic stability in fresh human whole blood and the distribution test in PBMCs of tenofovir prodrug are shown in Table 3.

TABLE 3

The results of the metabolic stability in fresh human whole blood and the distribution test in PBMCs cells of tenofovir prodrug

| Incubation duration | Analyte | GS-7340 | | Ia1 | |
| --- | --- | --- | --- | --- | --- |
| | | Prototype concentration (μM) | PAMA* concentration (μM) | Prototype concentration (μM) | PAMA* concentration (μM) |
| 0 hour | Initial concentration | 16.9 | 0 | 12.4 | 0 |
| 1 hour | In Plasma | 14.5 | 0.71 | 12.3 | 0 |
| | In PBMCs | 2448 | 199 | 1528 | 320 |
| 2 hour | In Plasma | 13.0 | 1.37 | 12.2 | 0 |
| | In PBMCs | 2357 | 207 | 1282 | 546 |

*PAMA is the active metabolite-tenofovir of prodrug

4. Conclusion
As can be seen from Table 3, certain active metabolite-tenofovir was detected in plasma for the positive control GS-7340 after incubation with fresh human whole blood, and the active metabolite-tenofovir released in plasma increased significantly over the incubation time. However, no active metabolite-tenofovir was detected in plasma for the compound Ia1 of the present invention after incubation with fresh human whole blood, and the active metabolite-tenofovir was not always detected over the incubation time, which illustrates that the stability of compound Ia1 in plasma was significantly better than the positive control GS-7340. Therefore, compound Ia1 of the present invention has significant advantages in reducing toxic side effects resulting from tenofovir in plasma compared with the positive control GS-7340.

It also can be seen from Table 3 that the concentration of the active metabolite-tenofovir in peripheral blood mononuclear cells (PBMCs) for compound Ia1 of the present invention increased significantly over the incubation time, while the concentration of the active metabolite-tenofovir in peripheral blood mononuclear cells (PBMCs) for compound GS-7340 was almost the same. The concentration of active metabolite-tenofovir in PBMCs for compound Ia1 was about three times of that for the positive control of GS-7340 after incubation for 2 hours. Thus, compound Ia1 of the present invention has significant advantages in terms of therapeutic effect compared with the positive control GS-7340.

Example 14: Anti-AIDS (HIV) Virus Test

1. Objective: To evaluate anti-HIV activity and cytotoxicity, and EC50 and CC50 value of three compounds.

2. Materials and Method

2.1 Materials

Compound: Compound Ia1, GS-7340, and tenofovir disoproxil
RPMI medium (Invitrogen 21969-035)
DMEM medium (Invitrogen 21969-035)
Glutamic acid 200 mM (Invitrogen 25030)
Fetal bovine serum ((Invitrogen 16000-044)
Penicillin/streptomycin ((Invitrogen 15140-122)
DPBS buffer (Invitrogen 14190-094)
Trypsin-EDTA (Invitrogen 25200)
Trypan blue Sigma T8154
DMSO Sigma D2650
MUG Biochemika 69590

2.2 Test Method

1) MT-2 cells were infected with HIV-1 (IIIb) to form multiplicity of infection (MOI) 0.01 $TCID_{50}$ per cell.
2) The mixture of virus and cells was incubated in a 384-well plate for 3 days.
3) Cells for the cytotoxic detection were incubated in a 384-well plate for 3 days.
4) The supernatant was transferred to a new plate and incubated with reporter cells (HeLa) for 24 hours.
5) Detecting beta-GAL activity to evaluate anti-HIV activity.
6) Luminescent signal of the cells free of virus was detected to evaluate cytotoxicity after incubation for 3 days.
7) The antiviral activity and cytotoxicity were calculated according to the following equation:

Antiviral activity (%)=100−(Detection value−Maximum value)/(Minimum value−Maximum value)*100

Cytotoxicity (%)=100−(Detection value−Maximum value)/(Minimum value−Maximum value)*100

8) $EC_{50}$ and $CC_{50}$ were calculated with Fit Curve of Graphpad Prism 5 (the results are shown in Table 4).

TABLE 4

The results of anti-HIV activity and cytotoxicity

| Compounds | $EC_{50}$(nM) | Toxicity $CC_{50}$(mM) |
|---|---|---|
| Positive control (GS-7340) | 12 | >150 |
| Positive control (Tenofovir Disoproxil) | 11 | 16.9 |
| Ia1 (chiral) | 8 | >150 |

3. Conclusion

The above results show that compound Ia1 has a strong inhibitory effect on HIV virus with no cytotoxicity.

The present invention has been described and illustrated by specific embodiments. Certain modifications and equivalent variations are apparent for those skilled in this art and are included within the scope of the present invention.

The invention claimed is:

1. A chiral compound of formula (I) or a stereoisomer, pharmaceutically acceptable salt, hydrate, or solvate thereof:

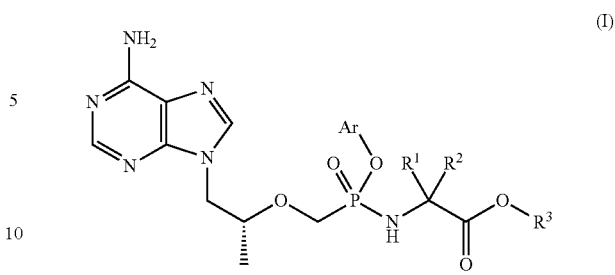

wherein:
  $R^1$ and $R^2$ are each methyl, or $R^1$ and $R^2$ together with the attached carbon atom form a $C_3$ cycloalkyl;
  $R^3$ is hydrogen, $C_{1-6}$ alkyl, substituted or unsubstituted $C_{6-10}$ aryl, or 6- to 10-membered heteroaryl; and
  Ar is substituted or unsubstituted $C_{6-10}$ aryl, or 6- to 10-membered heteroaryl.

2. The chiral compound of formula (I) according to claim 1, or the stereoisomer, pharmaceutically acceptable salt, hydrate, or solvate thereof, wherein the stereoisomer is selected from the group consisting of a tautomer, cis-trans isomer, conformational isomer, mesomer, an enantiomeric optical isomer, and a diastereomeric optical isomer.

3. The chiral compound of formula (I) according to claim 1, or the pharmaceutically acceptable salt thereof, wherein the compound is:

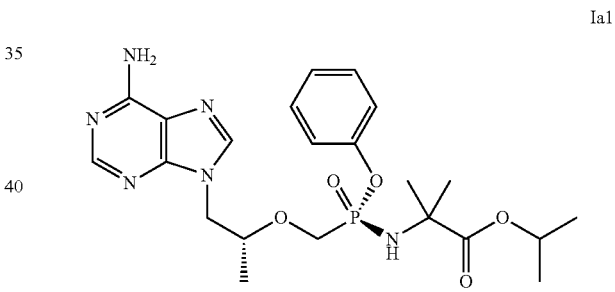

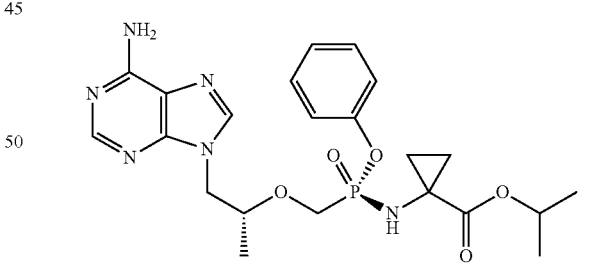

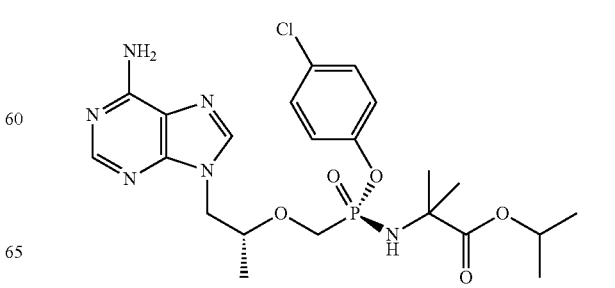

Id1

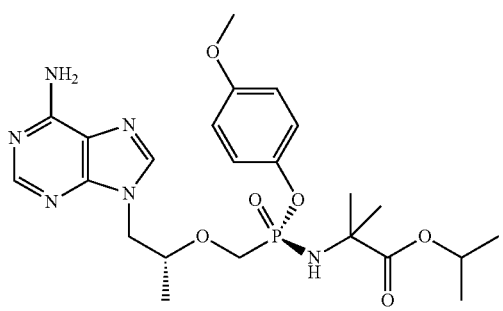

Ie1

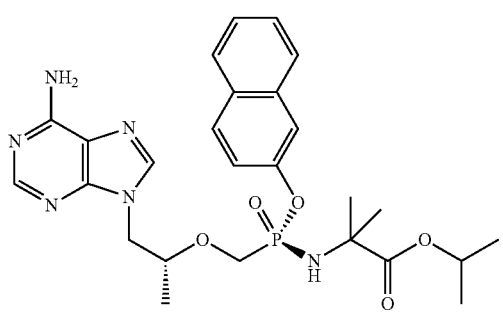

If1

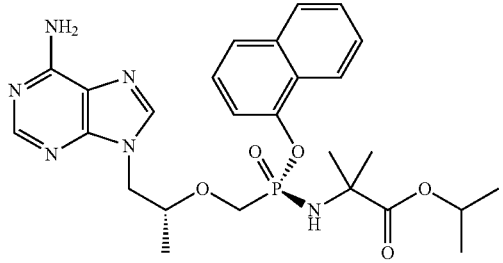

Ig1

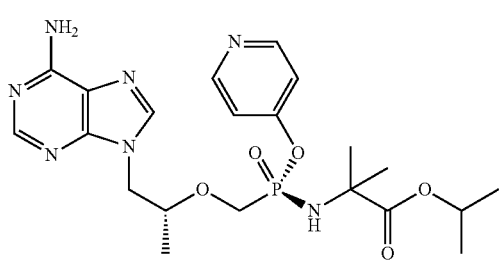

Ih1

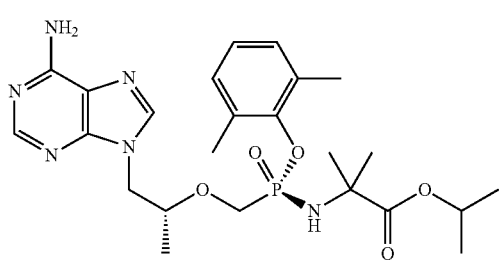

Ii1

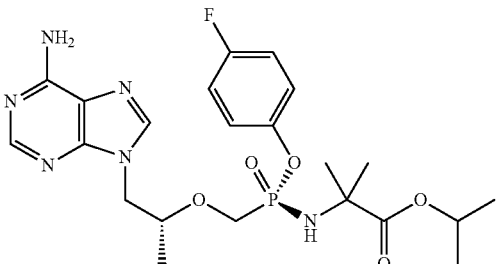

Ij1

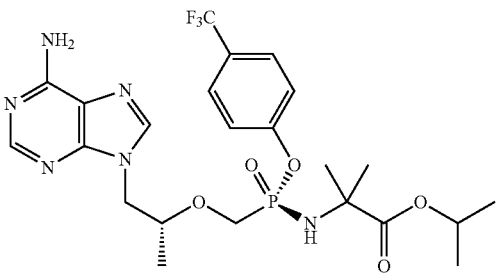

or

Ik1

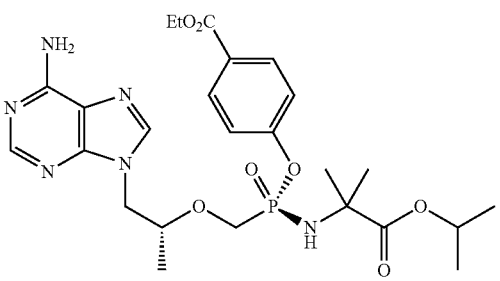

4. A chiral compound of formula (Ia1) or a pharmaceutically acceptable salt thereof:

Ia1

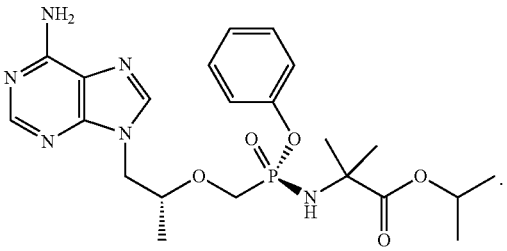

5. A pharmaceutical composition comprising the chiral compound of formula (I) or the stereoisomer, pharmaceutically acceptable salt, hydrate, or solvate thereof according to claim 1 and a pharmaceutically acceptable carrier.

6. The pharmaceutical composition according to claim 5, wherein the pharmaceutically acceptable carrier is selected from the group consisting of water for injection, lyophilized powder excipient, and oral preparation excipient.

7. A pharmaceutical composition comprising the chiral compound of formula (Ia1) or the pharmaceutically acceptable salt thereof according to claim 4 and a pharmaceutically acceptable carrier.

8. The pharmaceutical composition according to claim 7, wherein the pharmaceutically acceptable carrier is selected from the group consisting of water for injection, lyophilized powder excipient, and oral preparation excipient.

9. A pharmaceutical composition comprising the chiral compound of formula (I) or the pharmaceutically acceptable salt thereof according to claim 3 and a pharmaceutically acceptable carrier.

10. A method of treating a viral infection in a subject in need thereof, the method comprising administering to the subject the pharmaceutical composition according to claim 5.

11. The method according to claim 10, wherein the viral infection is selected from the group consisting of HIV infection, hepatitis B, and diseases caused by hepatitis B virus.

12. A method of treating a viral infection in a subject in need thereof, the method comprising administering to the subject the pharmaceutical composition according to claim 7.

13. The method according to claim 12, wherein the viral infection is selected from the group consisting of HIV infection, hepatitis B, and diseases caused by hepatitis B virus.

14. A method of treating a viral infection in a subject in need thereof, the method comprising administering to the subject the pharmaceutical composition according to claim 9.

15. The method according to claim 14, wherein the viral infection is selected from the group consisting of HIV infection, hepatitis B, and diseases caused by hepatitis B virus.

16. The chiral compound according to claim 1, or the stereoisomer, pharmaceutically acceptable salt, hydrate, or solvate thereof, wherein $R^1$ and $R^2$ are each methyl.

* * * * *